(12) United States Patent
Pruneri et al.

(10) Patent No.: US 10,346,972 B2
(45) Date of Patent: Jul. 9, 2019

(54) IMAGE CYTOMETER FOR CHARACTERIZATION AND QUANTIFICATION OF PARTICULATE SAMPLES

(71) Applicants: Fundació Institut de Ciències Fotòniques, Castelldefels (Barcelona) (ES); Institució Catalana de Recerca I Estudis Avançats, Barcelona (ES)

(72) Inventors: Valerio Pruneri, Castelldefels (ES); Marc Jofre, Castelldefels (ES); Juan Miguel Perez Rosas, Castelldefels (ES)

(73) Assignees: FUNDACIO INSTITUT DE CIENCIES FOTONIQUES, Barcelona (ES); INSTITUCIO CATALANA DE RECERCA I ESTUDIS AVANCATS, Barcelona (ES)

(*) Notice: Subject to any disclaimer, the term of this patent is extended or adjusted under 35 U.S.C. 154(b) by 74 days.

(21) Appl. No.: 15/136,303

(22) Filed: Apr. 22, 2016

(65) Prior Publication Data
US 2016/0313231 A1 Oct. 27, 2016

(30) Foreign Application Priority Data
Apr. 23, 2015 (EP) .................................... 15164853

(51) Int. Cl.
*G01N 15/00* (2006.01)
*G01N 15/10* (2006.01)
(Continued)

(52) U.S. Cl.
CPC ....... *G06T 7/0012* (2013.01); *G01N 15/1463* (2013.01); *G01N 15/1468* (2013.01); *G01N 21/6428* (2013.01); *G01N 21/6456* (2013.01);

*G02B 21/0008* (2013.01); *G02B 21/365* (2013.01); *G06T 7/0014* (2013.01);
(Continued)

(58) Field of Classification Search
USPC ...... 422/73; 436/10; 382/128, 133, 134, 280
See application file for complete search history.

(56) References Cited

U.S. PATENT DOCUMENTS

| 2004/0136577 A1* | 7/2004 | Rao ........................ G02B 27/46 382/128 |
| 2012/0156714 A1* | 6/2012 | O'Brien ................ G01J 3/2803 435/29 |

FOREIGN PATENT DOCUMENTS

| EP | 2 187 198 A1 | 5/2010 |
| WO | WO 2008/092074 A1 | 7/2008 |

(Continued)

OTHER PUBLICATIONS

European Search Report dated Oct. 23, 2015 issued in corresponding European patent application No. 15 16 4853.
(Continued)

*Primary Examiner* — Dean Kwak
(74) *Attorney, Agent, or Firm* — Ostrolenk Faber LLP

(57) ABSTRACT

An image cytometer for capturing and analyzing the image of a sample in the momentum domain. The cytometer is provided with a light source for illuminating a sample with a light beam, an optical transforming system positioned behind the sample in the beam propagation direction for generating the Fourier transform in the space plane, a light sensor array and a spatially selective filter positioned with respect to the optical system such that the Fourier transform is imaged onto the light sensor array.

12 Claims, 10 Drawing Sheets

(51) Int. Cl.
*G01N 15/14* (2006.01)
*G01N 21/64* (2006.01)
*G06T 7/00* (2017.01)
*G02B 21/00* (2006.01)
*G02B 21/36* (2006.01)

(52) U.S. Cl.
CPC ........... *G01N 2015/0065* (2013.01); *G01N 2015/1006* (2013.01); *G01N 2201/062* (2013.01); *G01N 2201/068* (2013.01); *G01N 2201/12* (2013.01)

(56) References Cited

FOREIGN PATENT DOCUMENTS

| WO | WO 2008092074 A1 * | 7/2008 | ........... G02B 21/361 |
|----|---|---|---|
| WO | WO 2009/020977 A1 | 2/2009 | |
| WO | WO 2013/065035 A1 | 5/2013 | |
| WO | WO 2013065035 A1 * | 5/2013 | ........... G01J 3/0256 |
| WO | WO 2014/018584 A1 | 1/2014 | |

OTHER PUBLICATIONS

Goodman, *Introduction to Fourier Optics*, 2nd Edition, pp. 73-75 and 101-107, 1996.

* cited by examiner

IMAGE CYTOMETER FOR CHARACTERIZATION AND QUANTIFICATION OF PARTICULATE SAMPLES

FIELD OF THE INVENTION

The present invention relates to optical devices, more particularly, an image cytometer.

BACKGROUND OF THE INVENTION

Optical technologies can be very powerful when it comes to detecting minute quantities of particulate in biological and pathogenic samples. More specifically, optical microscopy is also widely used in combination with fluorescence labeling for high resolution imaging of particulates (cells, microorganisms, etc.) in large laboratories and clinics. Fluorescent microscopes on the market are bulky and expensive due to their cumbersome assembly and high cost of optical elements forming them. Over the past few years, efforts have been made to find more compact and inexpensive imaging solutions to meet market needs by making use of low cost imaging technologies based on charge-coupled devices (CCD) or complementary metal-oxide-semiconductor (CMOS) sensor arrays.

Flow cytometry is a well-known laser based fluorescence technique that has experienced significant growth and innovation in recent years. This analytical laboratory technique can rapidly and very reliably measure different parameters on single cells and particles. Advances in the use of charge-coupled devices (CCD) have great potential in lowering prices by substituting expensive laser sources with much less expensive, up to two orders of magnitude, light-emitting diodes and sophisticated microscopes with simpler and more economic proximity detection schemes. These devices are known as image cytometers (I-CYTS) and can be easily operated through direct cell imaging on a computer screen. Unlike flow cytometers, I-CYTs do not work by illuminating the cells with a laser one by one but rather by imaging and analyzing thousands of cells in a single picture. For these reasons I-CYTs are gradually entering the market as they offer similar characteristics and benefits as conventional flow cytometers do but at a lower cost. U.S. Pat. Nos. 8,866,063 and 7,872,796 disclose microscope systems that use an image sensor, as is also the case for an image cytometer, that detect an image which is the replica of the sample in the space domain (known as the real or coordinate space). However, detecting the image in the space domain implies a tradeoff between spatial resolution, field of view (FOV) and depth of field (DOF). Resolution in optical microscope systems is limited by the diffraction limit (of the order of the wavelength of the light source, $\lambda$). In U.S. Pat. No. 7,872,796, a lenslet array is used to increase DOF of the device. However, FOV is still limited by the microscope objective in the system; therefore a $\lambda/2$ resolution can potentially be achieved with the device therein disclosed, but for reduced FOV. U.S. Pat. No. 8,866,063 describes a device with improved FOV by using an illumination source configured to scan the sample in at least two dimensions, capturing images in a plurality of scan locations. However, DOF is limited and the proposed solution to increase FOV implies lengthy computation to reconstruct the sample from the plurality of images captured; it also requires a cumbersome mechanical adaptation to provide the light source scanning.

BRIEF DESCRIPTION OF THE INVENTION

The present invention captures and analyzes the image of the sample in the spatial frequency domain (also known as momentum domain or Fourier domain), in a plane that contains spatial frequency information. The real (space) image can then be reconstructed through Fourier analysis. The term "frequency" instead of "spatial frequency" will be used hereinafter.

For this purpose, the present invention is provided with a light source for illuminating a sample with a light beam, an optical transforming system positioned behind the sample in the beam propagation direction for generating the Fourier transform in the space plane, a light sensor array and a spatially selective filter positioned with respect to the optical transforming system such that the Fourier transform is imaged onto the light sensor array.

Given that sample information is retrieved through data in the frequency domain instead of the space domain, the invention is capable of analyzing large volumes (from one to ten milliliters) in a single capture as a result of a combination of a large FOV and DOF, automatically and accurately estimating the concentration of the particulate and differentiating population in terms of size and complexity (absorbance). Furthermore, with the disclosed system, spatial resolution can reach sub-micron resolution for a wide field of view choosing the proper light sensor array, doing so without the need for any mechanical adaptation or complex computation.

BRIEF DESCRIPTION OF THE DRAWINGS

A set of drawings is attached to complete the description and to provide for better understanding of the invention. Said drawings illustrate a preferred embodiment of the invention, which should not be interpreted as restricting the scope of the invention, but merely as an example of how the invention can be embodied.

DETAILED DESCRIPTION

Figure 1:
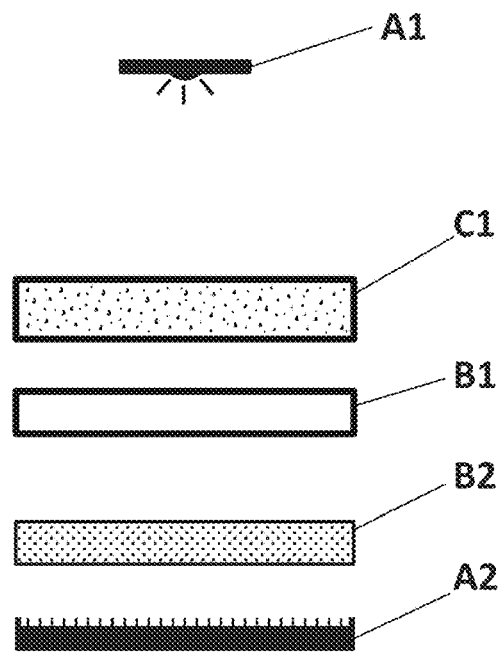
FIG. 1 shows a general implementation of the invention.

The invention works as follows. The sample is illuminated by a light source. For a given sample volume, interaction of said volume with the light source results in the emission of a broad band of frequencies. The emission process is incoherent; thus the intensities sum up and do not give rise to interference effects. The sample is placed in front of and in proximity to an optical transforming system (OTS). The OTS is an essential part, as it allows retrieving the Fourier transform of the beam generated by interaction between the sample volume and light beam. Examples of possible OTSs are a lens, a curved mirror with a radius of curvature equal to twice the focal length of a lens or a pinhole.

Finally, a spatially selective filter is placed after the OTS at a distance suitable for achieving the Fourier transform of the beam interacting with the sample. The incoming beam is divided into regions in the XY plane through sampling with the sub-structures of the spatially selective filter, thus creating a set of sub-images; in other words, frequency information is selectively contained in the sub-images. Spatial sampling consists of the sub-images produced by the spatially selective filter and detected by the corresponding light sensors. The sensor array is located right after and in proximity to the spatially selective filter. The resulting image will be a composition of all the sub-images, each one containing a part of the Fourier transform of the beam after interaction with the sample volume. A measure on the resulting intensity distribution of these sub-images implies knowledge of the sample's energy spectrum.

A preferred embodiment of the OTS is a converging lens. Such a lens inherently performs a two-dimensional Fourier transform, as will be explained. Consider the general geometry where a sample, located in front of the lens, is illuminated by a normally incident plane wave of amplitude A. Amplitude transmittance of the sample is represented by $t_A$. In this case, the beam leaving the sample and incident on the lens can be described as:

$$U_L(x,y) = A \cdot t_A(x,y)$$

The effects of the lens on the incident optical beam due to the optic can be described by:

$$t_l(x,y) = \exp[-j \cdot (k/2 \cdot f) \cdot (x^2 + y^2)]$$

Amplitude distribution behind the lens therefore becomes $$U_L'(x,y) = U_L(x,y) \cdot \exp[-j \cdot (k/2 \cdot f) \sim (x^2 + y^2)]$$

Using the Fresnel diffraction formula, one can find the distribution $U_f(u,v)$ at a distance z from the lens.

$$U_f(u,v) = \{\exp[j \cdot (k/(2 \cdot z)) \cdot (u^2 + v^2)] \cdot (1/(j \cdot \lambda \cdot z)) \cdot \iint U_L(x,y) \\ \cdot \exp[-j \cdot (k/2 \cdot f) \cdot (x^2 + y^2)] \cdot \exp[j \cdot (k/(2 \cdot z)) \cdot (x^2 + y^2)] \\ \cdot \exp[-j \cdot (2\pi/(\lambda \cdot z)) \cdot (x \cdot u + y \cdot v)] dx dy$$

Field distribution $U_f(u,v)$ is therefore proportional to the two-dimensional Fourier transform of the incident field subtended by lens aperture with a quadratic phase factor, and the amplitude and phase of the light at coordinates (u, v) are related to the amplitude and phase of the input spectrum at frequencies (u/λf), v/(λf)).

Let the converging lens have a focal length "f". The sample volume is assumed to be uniformly illuminated by a normally incident beam from the light source. After the lens, complex field distribution is proportional to the two-dimensional Fourier transform within the lens aperture. The amplitude and phase of the light field that has traversed the sample volume in the spatial domain can then be reconstructed from the amplitude and phase of the measured Fourier components at frequencies (f'=u/(λ·f)). Therefore, it is possible to retrieve sample information from the measured power (energy) distribution after the OTS. Consider the following more specific geometry: the input sample volume, located at a distance "d", where "d" is much smaller than "f", in front of (in proximity to) the converging lens, is illuminated by a normally incident collimated beam. The Fourier transform of the beam after the sample volume is imaged at a distance "f" after the converging lens.

For a pinhole, transformation from the space domain into the frequency domain works as follows:

A plane wave of light incident upon an aperture [A(x)] will produce the Fourier transform of A(x) on the image plane. In particular, consider a diffracting aperture that is circular rather than rectangular, and let the radius of the aperture be w. Therefore, if q is a radius coordinate in the plane of the aperture, then $t_A(q) = \text{circ}(q/w)$. The circular symmetry of the problem suggests that the Fourier transform be rewritten as a Fourier-Bessel transform. Amplitude distribution in the Fraunhofer diffraction pattern is $$U(r) = A \cdot \exp[j \cdot k \cdot z] \exp[j \cdot k \cdot r^2/(2z)] \cdot (1/(j \cdot \lambda)) \cdot [2 \cdot J_1(k \cdot w \cdot r/z)/(k \cdot w \cdot r/z)],$$

where $J_1$ is the Bessel function of the first kind.

A curved mirror is equivalent to a lens when the radius of curvature of the mirror is equal to twice the focal length (f) of the lens.

Once the optical signal has been transformed by means of the OTS, an image is selected by means of a spatial filter. Examples of such a filter are apertures, a microlens array and an absorptive polymer mask, i.e., a two-dimensional array-like structure built of several apertures capable of spatially filtering an incoming beam. Each aperture selects a portion of the incoming beam preserving information about both its amplitude and phase. Sample information contained in the optical signal detected after the spatially selective filter can thereby be retrieved after suitable data processing of the image detected by the light sensor array. Multiple two-dimensional array-like structures are known to comply with the spatially selective filtering requirements to implement the disclosed invention; among them, a microlens array and an absorptive polymer mask made up of a transmitting well array are considered preferred solutions for this invention. The pitch of the lens array, polymer mask or any other structure complying with the specifications, will define the periodicity of the sub-images captured by the light sensor array. The aperture of the microlenses, wells or equivalent will define spatial filtering capabilities of the spatially selective filter.

In the case of a microlens array configuration, filtering capabilities are defined by the angular aperture of each microlens ($N_m$):

$$N_m = \frac{f_m}{D_m}$$

In the equation, "$f_m$" represents the focal length of each microlens and "$D_m$" its diameter.

A microlens is a small lens, generally with a diameter less than one millimeter (mm) and often as small as 10 micrometers (μm). A typical microlens may be a single element with one plane surface and one spherical convex surface to refract the light. Since microlenses are so small, the substrate that supports them is usually thicker than the lens. More sophisticated lenses may use aspheric surfaces, and others may use several layers of optical material to achieve the designed performance. Microlens arrays contain multiple microlenses formed in a one-dimensional or two-dimensional array on a supporting substrate. If the individual lenses have circular apertures and are not allowed to overlap, they may be placed in a hexagonal array to obtain maximum coverage of the substrate. However, there will still be gaps between lenses which can only be reduced by making microlenses with non-circular apertures. With optical sensor arrays, very small lens systems serve to focus and concentrate the light onto the photodiode surface instead of allowing it to fall on non-photosensitive areas of the pixel device. Fill-factor is the ratio of the active refracting area, i.e., that area which directs light to the detecting surface, to the total contiguous area occupied by the microlens array. The microlens array works as an array of point scanning microscope objectives over the optical Fourier transform of the volumetric sample.

In the case of an absorptive polymer mask, the filtering effect can be described as follows:

$$\tan \varphi_m = \frac{d_m}{L_m}$$

In the equation, "$d_m$" represents the diameter of the mask aperture element, "$L_m$" the height of the mask and the angle phi, "$\varphi_m$", represents the acceptance angle with respect to the normal which is inherently linked to the spatial frequencies of the incoming beam.

An absorptive polymer mask is a well array with a pitch equivalent to that of the microlens array but apertures (1% to 30%) smaller than the diameter of the lenses, thus providing a robust structure. The height of the mask defines filtering capabilities. Said height should be within a range that avoids both aliasing and under-sampling; it should preferably result in an aspect ratio between the height of the mask and the well aperture ($AR=L_m/d_m$) from 1 to 10, which is equivalent to an acceptance angle from 6 to 45 degrees. An acceptance angle below 6 degrees may result in under-sampling the optical signal and therefore not enough information for sample recovery, while an acceptance angle higher than 45 degrees may result in serious detrimental aliasing. The thicker the mask (increase in height), the more selective the structure. However, there is a tradeoff between high selectivity and under-sampling of the signal which would result in loss of information.

Finally, the resulting image is detected by means of a light sensor array. Examples of such an array are CODs, cameras in conventional mobile phones or any other portable devices, etc.

Data extraction is based on Fourier optics principles; the detected pattern intensity is given by the following equation:

$$I_{(x,y)} \approx \left[\frac{A}{2\lambda Z_i}\right]^2 \cdot sinc^2\left(\frac{2wy}{\lambda Z_i}\right)$$
$$\left\{sinc^2\left(\frac{2wx}{\lambda Z_i}\right) + \frac{m^2}{4}sinc^2\left[\frac{2w}{\lambda Z_i}(x+f_0\lambda Z_i)\right] + \frac{m^2}{4}sinc^2\left[\frac{2w}{\lambda Z_i}(x-f_0\lambda Z_i)\right]\right\}$$

In the case of two-dimensional geometry, this represents spatial frequency distribution. The center of the image is zero spatial frequency and each of the other intensity points ($n\lambda Z_i f_0$) represents a harmonic of the captured signal.

Each of the sub-images contains information about statistical parameters of the sample volume, such as particulate size and complexity, also allowing counting of particles. Complexity and size information can be paired into a dispersion graph to present the results to the user. Said dispersion graphs will allow differentiating multiple particulates within a single sample volume. The complexity parameter refers to a measure of the absorbance of the sample, i.e., how much of the incident beam is absorbed by the sample.

Different embodiments are shown below in reference to the drawings.

FIG. 1 shows a general schematic of the invention, comprising: a wavelength band-limited light source (A1), an optical transforming system (OTS) (B1), a spatially selective filter (B2), and a light sensor array (A2). The figure also indicates the position of the sample (C1) within the apparatus. The sample is to be placed between the light source and the OTS.

Figure 2:
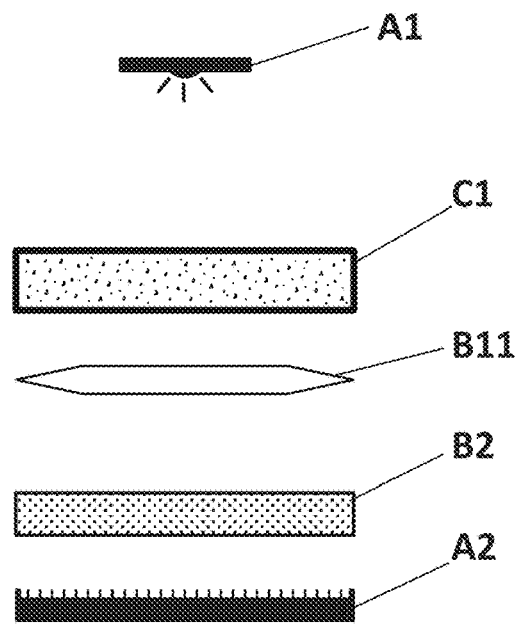
FIG. 2 shows one embodiment with an optical lens as the OTS.

In FIG. 2, an optical lens is used as the OTS (B11). The spatially selective filter (B2) is placed at the lens's angular frequency plane and the sample volume (C1) is placed in proximity to the OTS lens.

Figure 3:
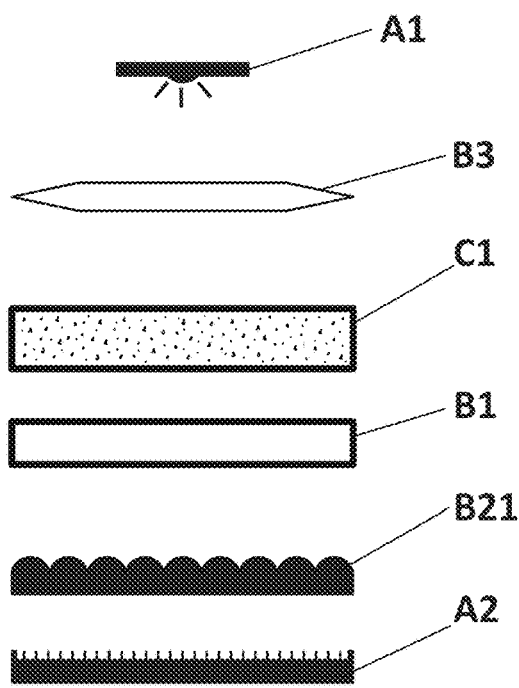
FIG. 3 shows a microlens array used in the invention as the spatially selective filter.

FIG. 3 shows an embodiment using a microlens array as a spatially selective filter and an optical lens to focus the light source onto the sample for improved illumination. The focusing optical lens (e.g. focal length of 50 mm) (B3) focuses the wavelength band-limited LED light source (A1) onto an area of the sample volume; the resulting beam is collected by the OTS (B1). The beam leaving the OTS is incident on the microlens array (B21), which decomposes the spatial Fourier transform components generated by the OTS (B1). Said array can have an area of 10 mm×10 mm array with a pitch of 300 μm for a total of 1111 microlenses and with a thickness of 1.2 mm. The light sensor array (A2) can be a commercially available CMOS image sensor with Bayer Filter technology, a size of 5.70 mm×4.28 mm and a pitch of 2.2 μm.

Figure 4:
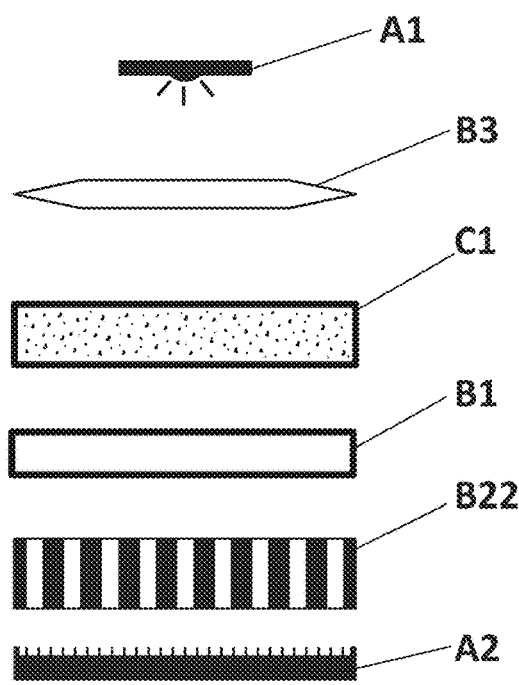
FIG. 4 shows an absorptive polymer mask as the spatially selective filter.

FIG. 4 shows another embodiment of the invention that uses an absorptive polymer mask instead of a microlens array in order to prevent or at least reduce aliasing effects in the detected signal. The rest of the components in the apparatus are the same as in the embodiment of FIG. 2. The absorptive polymer mask can be a structure measuring 10 mm×10 mm×6 mm (XYZ) made of a two-dimensional aperture array 250 μm in diameter and 300 μm in pitch. The resulting overall structure is made of 1111 different apertures each of which independently samples the incoming beam onto the light sensor array.

Figure 5:
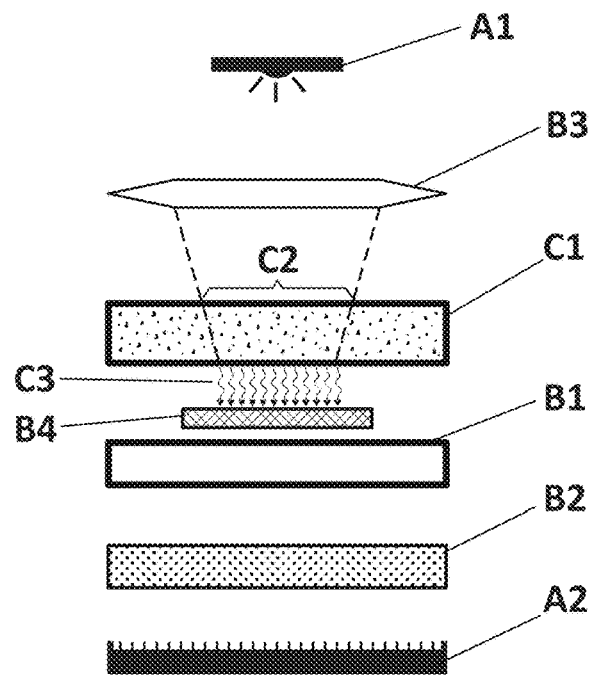
FIG. 5 shows one embodiment with a fluorescent filter.

One embodiment using a fluorescent filter is shown in FIG. 5. An appropriate fluorescent filter attenuates (absorbs) the pump light and lets the fluorescent signal be transmitted. This introduces an additional degree of specificity into the system, especially when size and/or complexity are not enough to differentiate between particulates. The system as described in FIG. 1 has been proven to differentiate particulates by size down to a 3 um difference; however, many biological samples to analyze might have several microorganisms of equal size. In this scenario, labeling and adding the fluorescent filter of FIG. 5 allows distinguishing the target microorganism. The focusing optical lens (B3) (e.g. focal length of 50 mm) focuses the wavelength band-limited LED light source (A1) onto an area of the sample volume (C2). This sample volume generates a fluorescent beam (C3) which is collected by an OTS (B1). The remaining pump signal is attenuated (filtered) by the fluorescent filter (B4), thereby leaving only fluorescent emission going through the spatially selective filter (B2) and detected by the light sensor array (A2).

Figure 6:
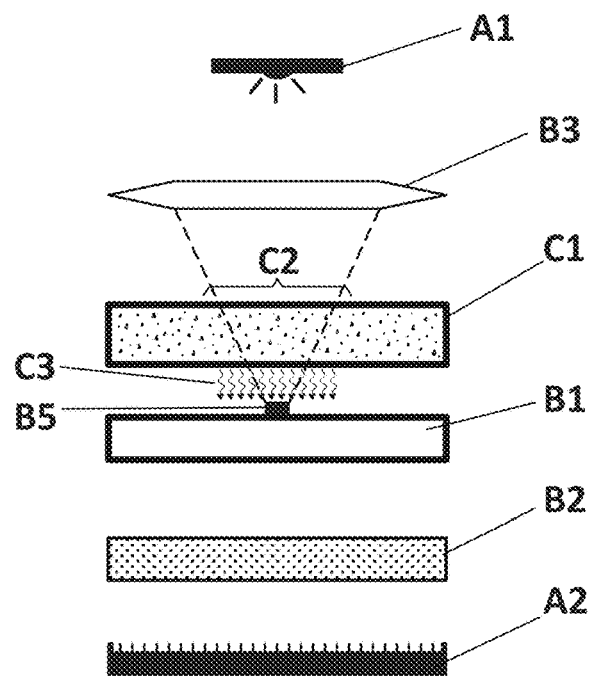
FIG. 6 shows another embodiment of a fluorescent cytometer according to the invention, with a reflective filter.

FIG. 6 shows another embodiment using a reflective filter (B5) to suppress the pump beam remaining after the sample volume. Rejection of the pump is especially important in the case of fluorescence detection. If the pump is rejected more than the fluorescent signal, a fluorescent filter might not be needed. Fluorescent emission is omnidirectional; therefore, even though some fluorescent signals will be reflected by the reflective filter, enough fluorescent intensity will reach the light sensor array (A2) so as to retrieve sample information from the capture.

Figure 7:
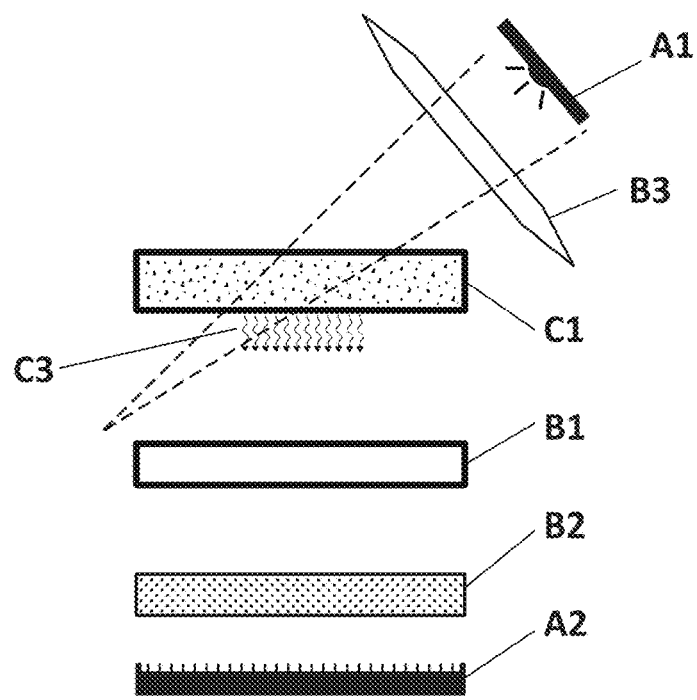
FIG. 7 shows one embodiment where the source is placed at an angle in order to avoid the use of filters.

In the embodiment of FIG. 7, the incident pump beam enters the sample volume at an angle. Use of filters can thereby be avoided.

Figure 8:
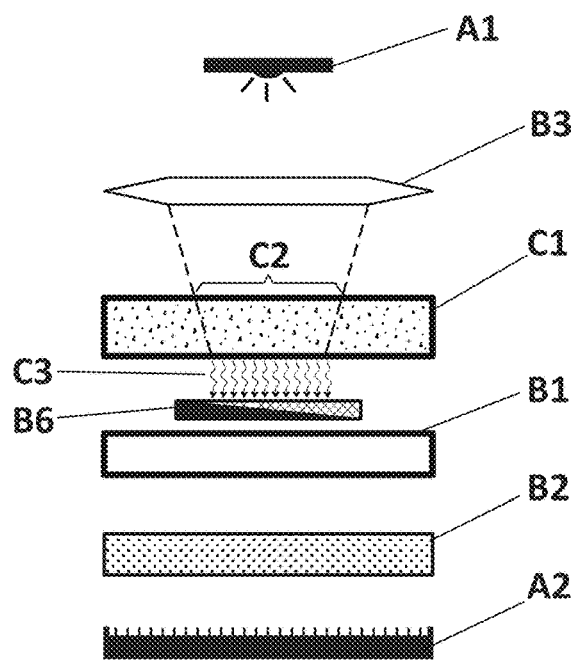
FIG. 8 shows one embodiment with dual-band fluorescent bandpass filter.

FIG. 8 shows a multi-fluorescent (dual-fluorescent) I-CYT configuration. The light source (A1) represents one or two wavelength band-limited LED light sources. A dual-band fluorescent bandpass filter (B6) is used, replacing the fluorescent filter in FIG. 5. More specifically, this system could be applicable to analyze a sample volume fluorescently marked with FITC (excitation and emission wavelengths of 495 nm and 519 nm, respectively) and PerCP (excitation and emission wavelengths of 470 nm and 670 nm, respectively) using a single LED light source centered within the excitation peaks and a 524 nm/676 nm dual-band fluorescent bandpass filter. Information can be singularized at the sensor by using a color image sensor and retrieving data from the corresponding color channel for each emitted wavelength. This introduces further specificity into the system, since particulates can now be sorted by complexity, size and fluorescence emission.

What has been said for fluorescence signals can be applied to autofluorescence geometries. This means in this case that the pump induces fluorescence directly from the particulate to detect without the need for fluorescent labeling. This is because the fluorescence from labels is attached to particulates and autofluorescence from the particulates themselves comes from the same sample volume regions, so the signal can be processed in the same way and the invention can thus be applied.

The operability of the invention allows to use standard optical chambers, cuvettes and fluidics (devices with no moving parts), to allocate the volume sample. An optical chamber or cuvette is a small tube of circular or square cross section, sealed at one end, made of plastic, glass, or fused quartz (for UV light) and designed to hold samples for experiments. Disposable plastic cuvettes are often used in fast assays, where speed is more important than high accuracy.

Furthermore, the raw sample can be filtered and purified while being concentrated using standard concentrator filters. Particulate concentrators are disposable, single use only ultrafiltration devices with polymer membranes for the concentration and/or purification of biological samples. The optical signal response of the invention to the number of particulates is linear, hence the invention requires a single value correction factor when using concentrator devices to better measure the real particulate concentration.

Figure 9:
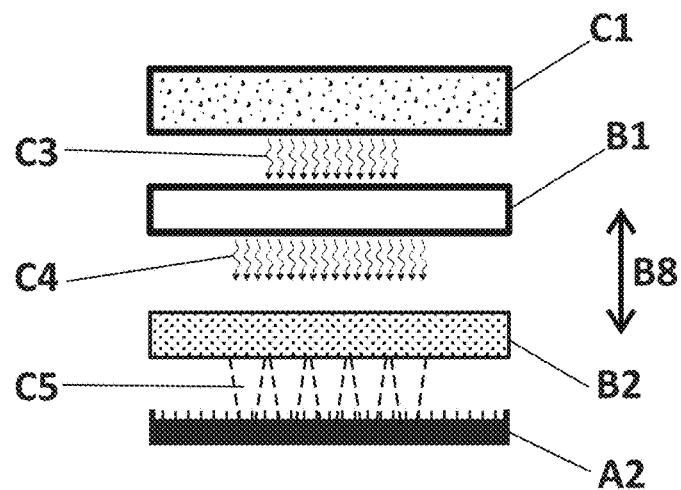
FIG. 9 schematically shows how data is processed.

FIG. 9 shows optical data processing. If the sample volume (C1) is placed in proximity to the OTS (B1), the principles of Fourier optics establish that at a distance (B8) from (B1), the position known as the spatial frequency plane or Fourier plane, the received signal (C4) will be equivalent to the Fourier transform of the input beam collected by the OTS (B1). By placing a spatially selective filter (B2) at said point (B8), several sub-images of the spatial Fourier transform will be generated, each of them corresponding to one sub-structure of the filter. A complete image made up of the aforementioned sub-images is captured at the sensor (A2).

Figure 10:
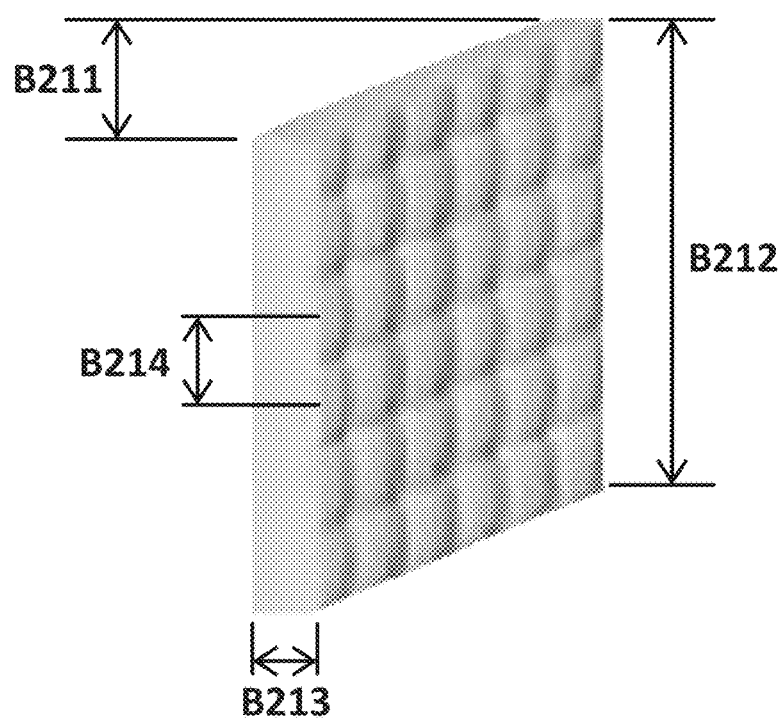
FIG. 10 shows a microlens array used in the invention.

A schematic of a microlens array (B21) used in one embodiment of the invention can be seen in FIG. 10. (B211) refers to the full size of the array in one direction, (B212) to the size in the orthogonal direction, (B213) indicates the thickness of the array and (B214) is the pitch between lenses. For the preferred embodiment of FIG. 2, the microlens array has a length of 10 mm along (B211), 10 mm along (212), 1.2 mm of thickness (B213) and a pitch (B214) of 300 μm, resulting in an array with a total of 1111 microlenses.

Figure 11:
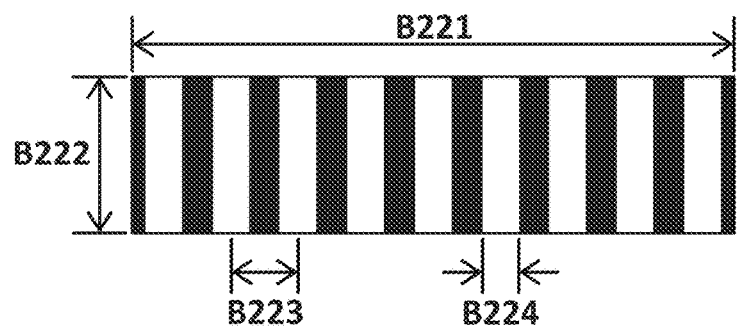
FIG. 11 shows an absorptive polymer mask used in the invention.

A schematic of the absorptive polymer mask (B22) used in one embodiment of the invention can be seen in FIG. 11. (B221) refers to the full size of the array in directions X and Y, (B222) refers to the size in the orthogonal Z direction, (B223) indicates the pitch between the apertures of the mask and (B224) the diameter of said apertures. For the preferred embodiment of FIG. 3, the absorptive polymer mask has a length of 10 mm along (B221), 6 mm along (B222), a pitch (B223) of 300 μm and an aperture size (B224) of 250 μm, resulting in a structure with a total of 1111 apertures.

Figure 12:
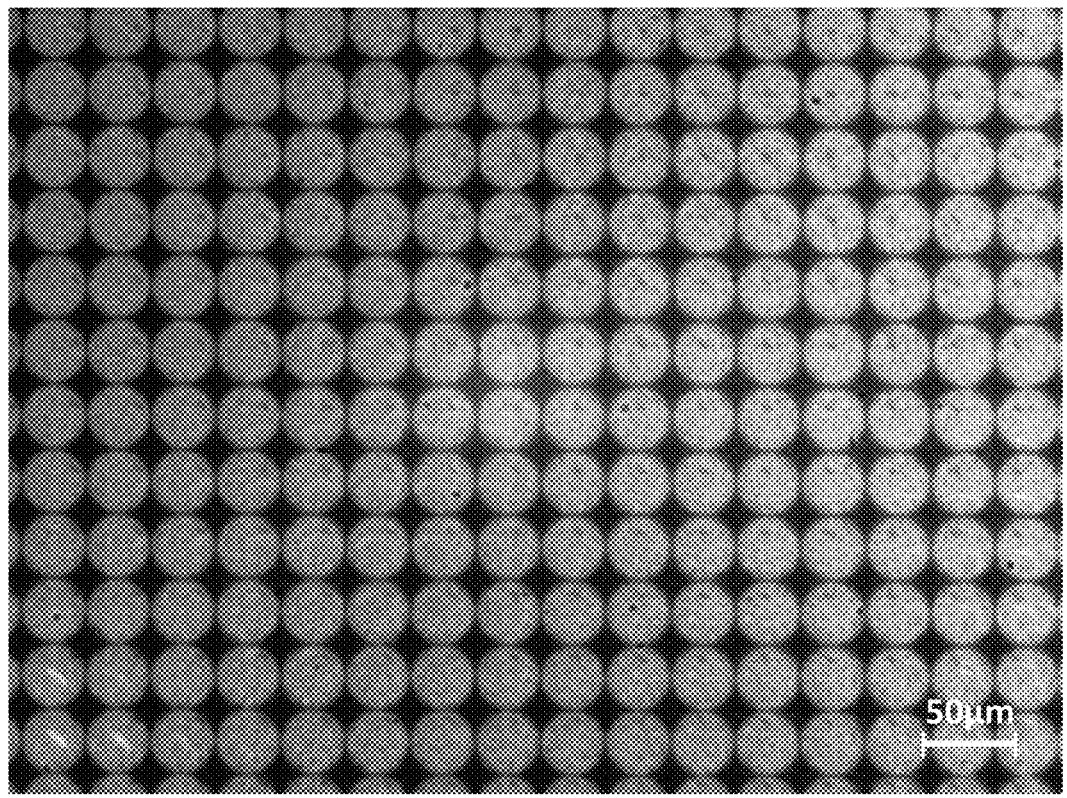
FIG. 12 shows raw capture from the embodiment of FIG. 3 proving the extended device FOV.

FIG. 12 shows a raw capture from the embodiment of FIG. 3, proving the extended device FOV. In the case of prior art for imaging applications, including light-field microscopy, FOV is dependent on the microscope objective used in the device. For example, for a 16× objective lens FOV is 1.3 mm$^2$. In the current invention, the sample is placed behind and very close to the lens capturing the Fourier transform. Hence, the magnification factor in the system is approximately 1. Therefore, the area of sample capture is equal to that imaged at the sensor, i.e. 5.70 mm×4.28 mm=24.39 mm$^2$, achieving a large FOV=24.39 mm$^2$. In contrast, in the prior art capturing images in real space means that the sample must be placed apart from the lens, and therefore a magnification factor greater than 1 reduces the effective field-of-view.

Figure 13:
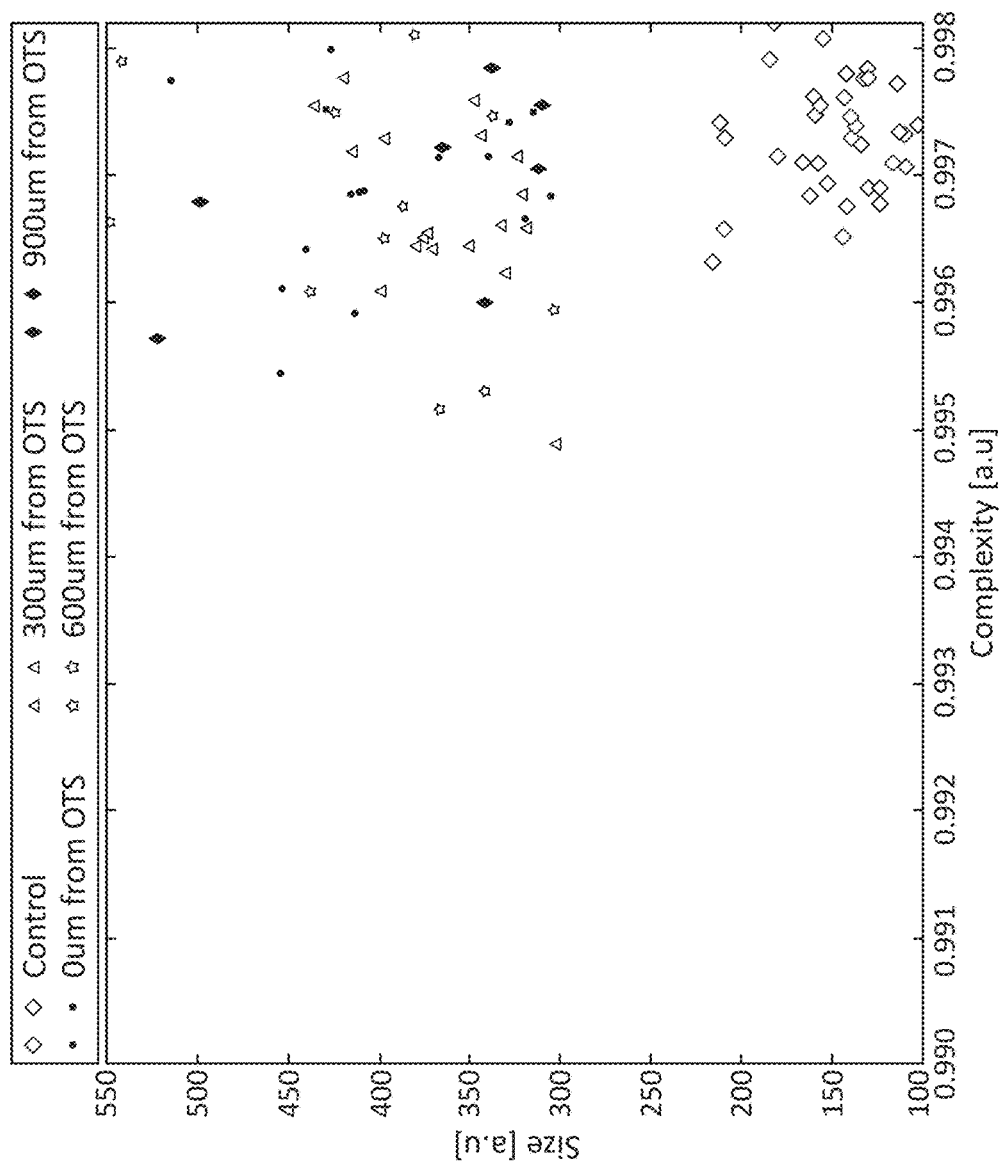
FIG. 13 shows how the same data is retrieved from the sample regardless of distance to the OTS, thus proving the large device DOF capability ($\approx$1 mm).

In FIG. 13 a sample of 5 μm particles was captured at several distances from the OTS and processed to retrieve sample size and complexity information. The resulting graph shown indicates how same data is retrieved from the sample regardless of its distance to the OTS, thus proving the large device DOF capability (≈1 mm). Detection of the particulate is repetitive in terms of the retrieved size and complexity information.

Figure 14:
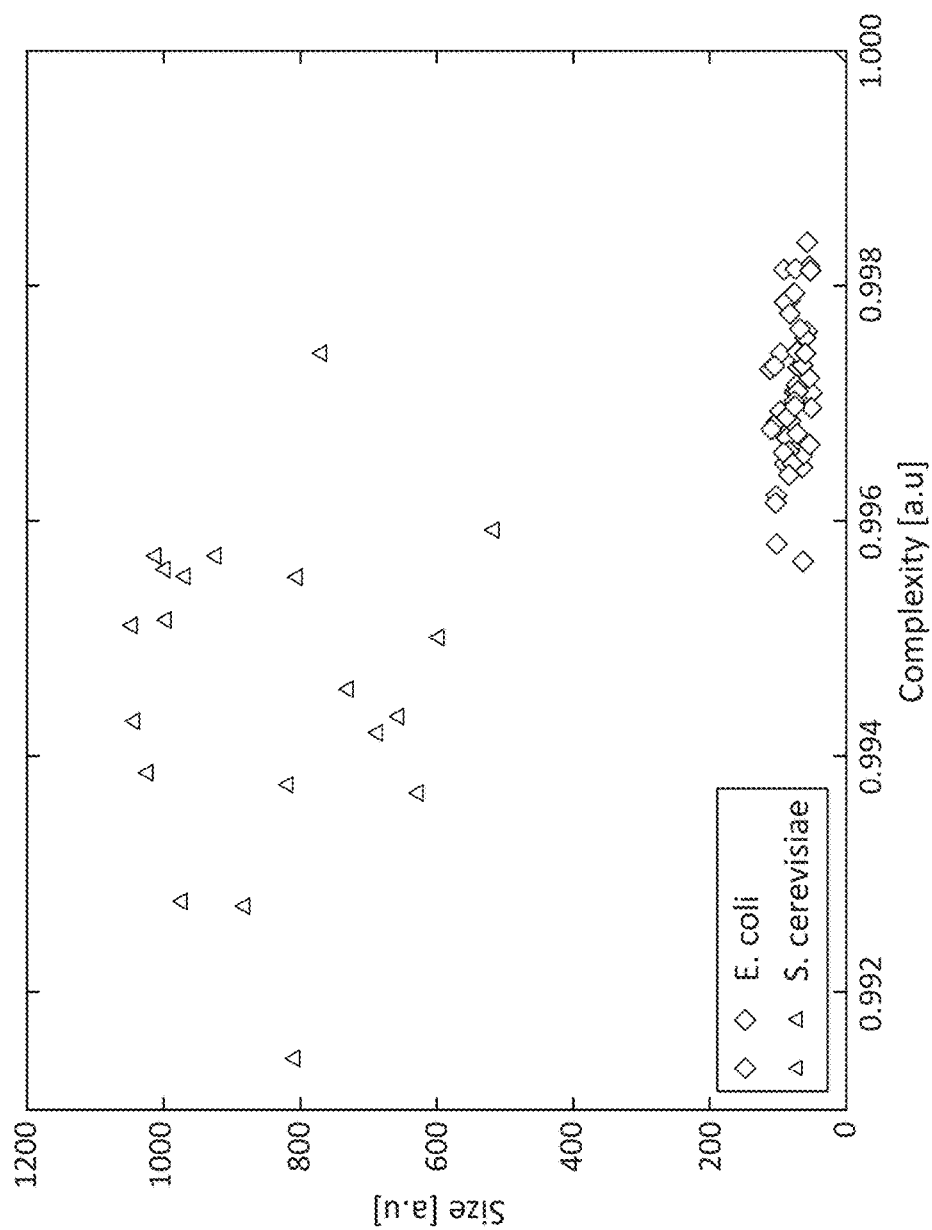
FIG. 14 shows a graph acquired from processing sample volumes of two different microorganisms captured with the embodiment of FIG. 3.
Figure 15:
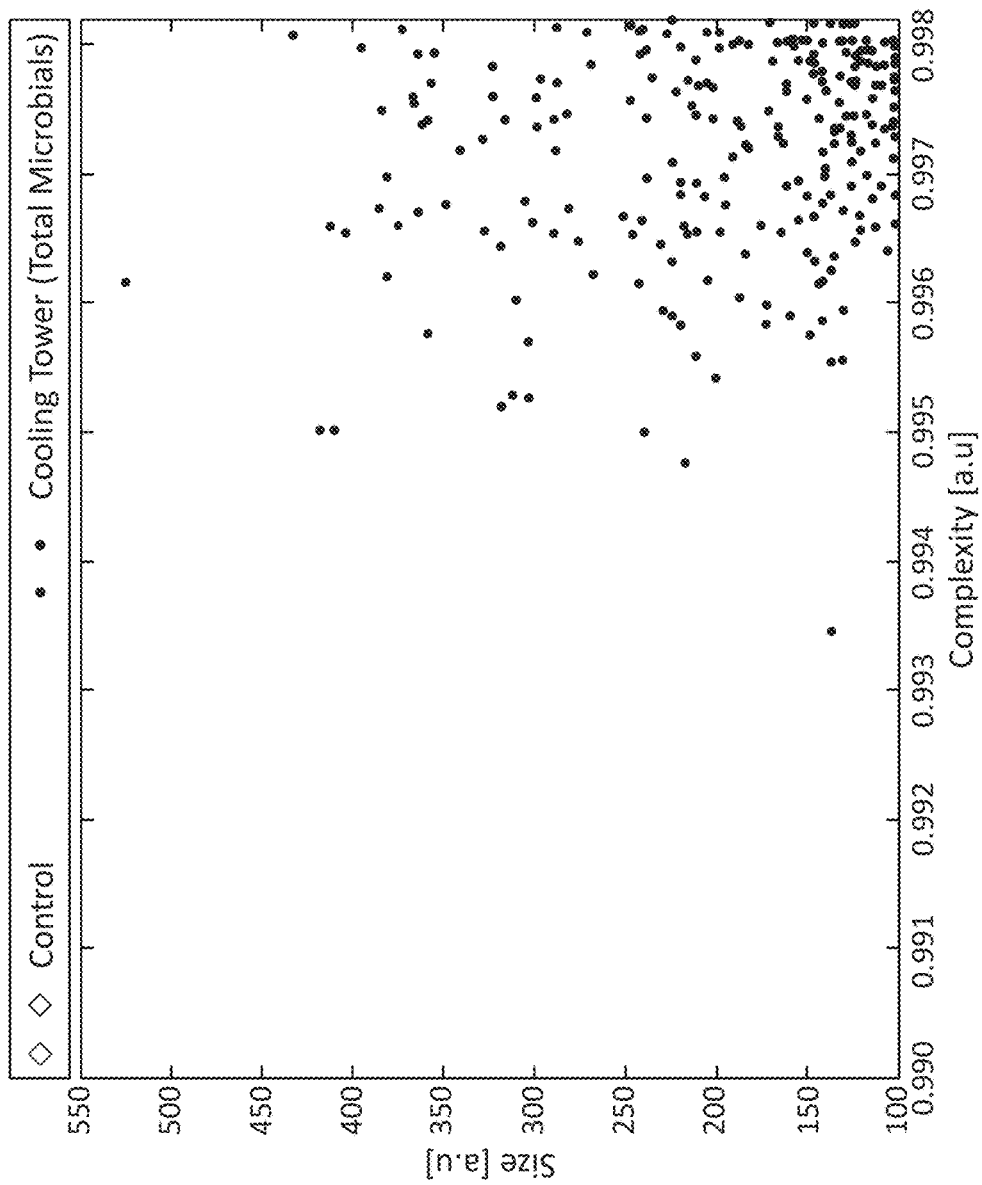
FIG. 15 shows a graph acquired from processing a water sample with a mixed population of microorganisms captured with the embodiment of FIG. 3.

FIG. 14 shows a dispersion graph acquired from processing two sample volumes captured with the embodiment of FIG. 3, in which the OTS (B1) is an optical lens (B11) as shown in FIG. 2. A sample of *Escherichia coli* (*E. coli*) at a concentration of 10$^4$ CFU/ml and a sample of *Saccharomyces cerevisiae* (*S. cerevisiae*) having a similar concentration, both diluted in phosphate buffered saline (PBS), were captured and processed. *E. coli* microorganisms are known to a have an average size of 2 μm, whereas *S. cerevisiae* have an average size of 5 μm. The graph displays complexity (horizontal axis) and size (vertical axis) of the particulate within the analyzed volumetric samples. From the graph it is evident that different microorganisms can be detected, characterized and differentiated in terms of their size and complexity parameters retrieved from the captured signal FIG. 15 depicts a dispersion graph acquired from processing a contaminated water sample captured with the embodiment of FIG. 3. The sample initially had an unknown variety of microorganisms. To ensure the presence of *E. coli*, 1 ml of a 10$^4$ CFU/ml *E. coli* concentration, diluted in PBS with anti-*E. coli* antibody conjugated to fluorescein isothiocyanate (FITC) fluorescent marker was added to 2 ml of a contaminated water sample. This process ensures fluorescently labeling the added $10^4$ CFU/ml concentration of *E. coli*. The resulting graph shows information corresponding to the complete microbiological load of the sample.

Figure 16:
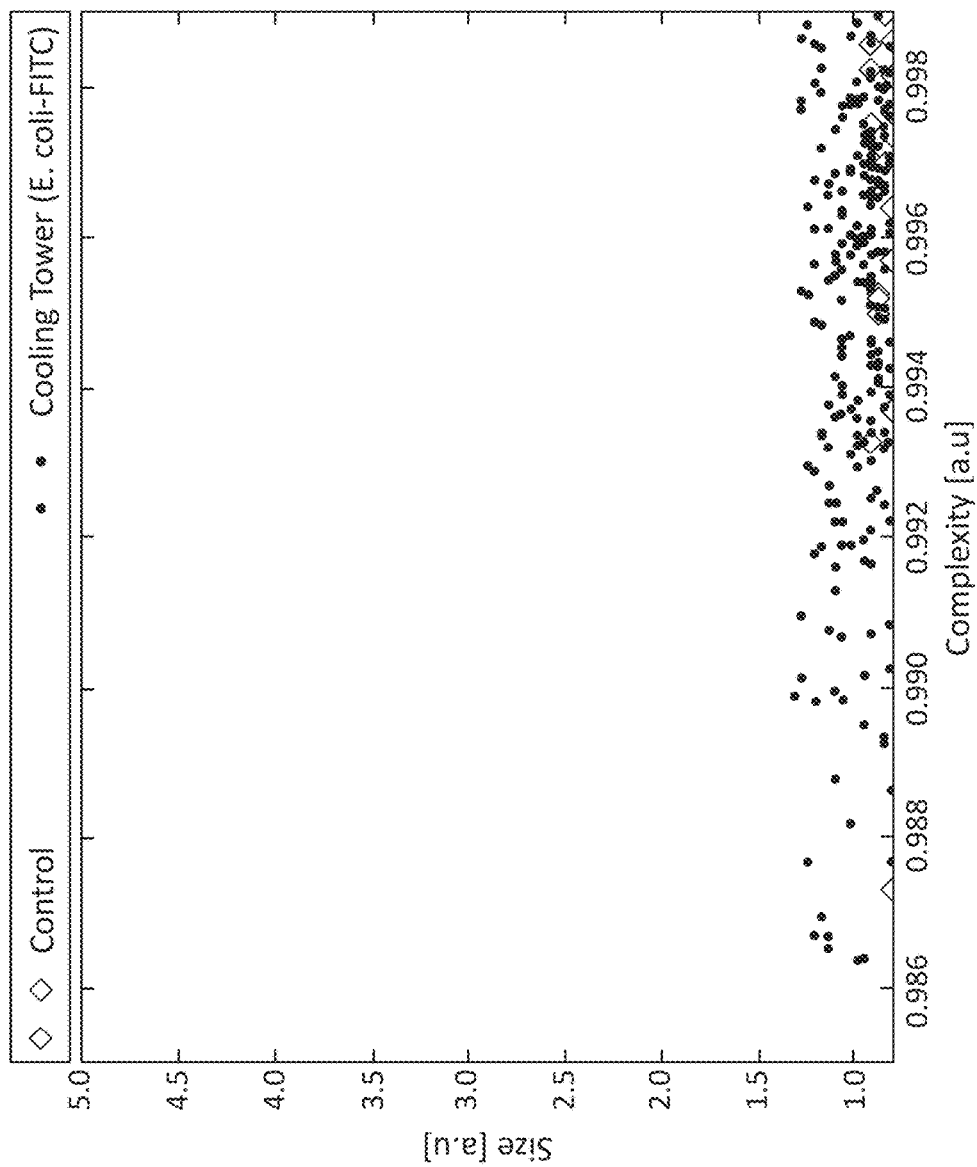
FIG. 16 shows a graph acquired from processing the water sample of FIG. 14, labeled with an anti-*E. coli* antibody conjugated to FITC and captured with the embodiment of FIG. 5.

FIG. 16 shows the dispersion graph corresponding to the same sample, this time captured with the embodiment of FIG. 5. In this case, only data corresponding to the FITC emitting *E. coli* microorganisms is retrieved.

In this text, the term "comprises" and its derivatives (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. An optical apparatus for characterization and quantification of particulate samples, comprising:
   a light source for generating an input beam directed towards a sample volume in a sample plane such that an optical signal in real space is generated after the beam traverses the sample volume;
   an optical transforming system positioned behind the sample volume for generating the Fourier transform of the optical signal in the spatial frequency domain, the optical transforming system being an optical lens, a curved mirror with a radius of curvature equal to twice the focal length of a lens or a pinhole;
   a spatially selective filter for obtaining separate sub-images of the Fourier transform, the spatially selective filter comprising a two-dimensional array of microlenses, each microlens having a diameter less than one millimeter, positioned on a supporting substrate at a multiple of the focal point of the optical transforming system, where the focal point is the point on the Fourier plane where light rays originating from a point on the Fourier plane converge;
   a light sensor array positioned at the focal point to detect a resulting image composed of all the sub-images, each sub-image containing a part of the Fourier transform after interaction with the sample volume, the resulting image characterizing and quantifying the articulate samples of the sample volume.

2. An optical apparatus according to claim 1, wherein the diameter of the microlenses are 10 micrometers.

3. An optical apparatus according to claim 1, wherein the spatially selective filter is an absorptive polymer mask.

4. An optical apparatus according to claim 3, wherein the absorptive polymer mask has wells of a pitch having less than one millimeter in depth, preferably 10 micrometers, with apertures 1%-30% smaller than the pitch.

5. An optical apparatus according to claim 3, wherein the height of the mask is between 1 mm and 10 mm.

6. An optical apparatus according to claim 1, wherein the light sensor array comprises a two-dimensional photodiode array for digitalizing the optical signal and processing means for retrieving information representative of the sample.

7. An optical apparatus according to claim 1, comprising an auxiliary optical lens after the sample to focus the optical signal onto the sensor array.

8. An optical apparatus according to claim 1, further comprising a fluorescent bandpass filter placed between the sample volume and the optical transforming system.

9. An optical apparatus according to claim 8, wherein the fluorescent filter is a multi-band fluorescent bandpass filter.

10. An optical apparatus according to claim 1, wherein the light sensor array consists of an image sensor of a mobile device such as a mobile phone, smart phone, smart tablet or a webcam.

11. An optical apparatus according to claim 1, wherein the sample is in an optically transparent chamber, cuvette or microfluidics container.

12. An optical apparatus according to claim 1, wherein the sample volume is adapted using a particulate filter and concentrator device.

* * * * *